US011344585B2

(12) United States Patent
Lefkowitz et al.

(10) Patent No.: US 11,344,585 B2
(45) Date of Patent: May 31, 2022

(54) COMPOSITIONS AND METHODS FOR DIAGNOSING SUSCEPTIBILITY TO AUTISM SPECTRUM DISORDER (ASD), REDUCING THE LIKELIHOOD OF DEVELOPING ASD, AND/OR TREATING ASD

(71) Applicant: FLAASK, LLC, University Heights, OH (US)

(72) Inventors: Andrew R. Lefkowitz, Solon, OH (US); Sean Farmer, North Miami Beach, FL (US); Ken Alibek, Solon, OH (US); Albina Tskhay, Solon, OH (US); Alibek Moldakozhayev, Solon, OH (US)

(73) Assignee: FLAASK, LLC, University Heights, OH (US)

( * ) Notice: Subject to any disclaimer, the term of this patent is extended or adjusted under 35 U.S.C. 154(b) by 0 days.

(21) Appl. No.: 16/639,634

(22) PCT Filed: Aug. 29, 2018

(86) PCT No.: PCT/US2018/048571
§ 371 (c)(1),
(2) Date: Feb. 17, 2020

(87) PCT Pub. No.: WO2019/046444
PCT Pub. Date: Mar. 7, 2019

(65) Prior Publication Data
US 2020/0179462 A1    Jun. 11, 2020

Related U.S. Application Data

(60) Provisional application No. 62/551,557, filed on Aug. 29, 2017.

(51) Int. Cl.
*A61K 35/742* (2015.01)
*A23L 33/175* (2016.01)
(Continued)

(52) U.S. Cl.
CPC .......... *A61K 35/742* (2013.01); *A23L 29/035* (2016.08); *A23L 33/105* (2016.08);
(Continued)

(58) Field of Classification Search
CPC ..................................................... A61K 35/742
See application file for complete search history.

(56) References Cited

U.S. PATENT DOCUMENTS

| 2011/0183019 A1 | 7/2011 | Theoharides |
| 2015/0258164 A1 | 9/2015 | Murdock et al. |
| 2016/0369357 A1 | 12/2016 | Taylor |

FOREIGN PATENT DOCUMENTS

| CN | 106389479 A | 2/2017 |
| WO | 2014046700 A1 | 3/2014 |

OTHER PUBLICATIONS

English machine translation of Tukahara, WO 2013/073644 A1, 2013.*
(Continued)

*Primary Examiner* — Rosanne Kosson
(74) *Attorney, Agent, or Firm* — Saliwanchik, Lloyd & Eisenschenk

(57) ABSTRACT

The present invention provides compositions and methods for improving the quality of life for a subject, particularly a child, diagnosed with autism spectrum disorder (ASD). In preferred embodiments, a supplement composition comprising natural or naturally-derived ingredients is delivered to a subject in the form of a chocolate bar or other candy alongside administration of an antiviral medication. Advantageously, the composition and methods can improve the immune health of the subject, along with other signs and symptoms associated with ASD, infections and other immunocompromising conditions.

10 Claims, 1 Drawing Sheet

(51) Int. Cl.
*A23L 33/105* (2016.01)
*A23L 33/135* (2016.01)
*A61P 25/00* (2006.01)
*A61K 31/198* (2006.01)
*A61K 31/522* (2006.01)
*A61K 36/35* (2006.01)
*A61K 36/481* (2006.01)
*A61K 36/63* (2006.01)
*A23L 29/00* (2016.01)
*A23L 33/00* (2016.01)
*A61K 36/48* (2006.01)
*A61K 9/00* (2006.01)

(52) U.S. Cl.
CPC .......... *A23L 33/135* (2016.08); *A23L 33/175* (2016.08); *A23L 33/30* (2016.08); *A61K 31/198* (2013.01); *A61K 31/522* (2013.01); *A61K 36/35* (2013.01); *A61K 36/48* (2013.01); *A61K 36/481* (2013.01); *A61K 36/63* (2013.01); *A61P 25/00* (2018.01); *A61K 9/0056* (2013.01)

(56) References Cited

OTHER PUBLICATIONS

Bahmani et al., "Autism: phathophysiology and promising herbal remedies," Current Pharmaceutical Design 22:1-9, 2016.*

Sun et al., "Analysis and evaluation on fatty acid compositions of wild oil source plants rich in linolenic acids in Changbai Mountain area," World Automation Congress, Conference of Jun. 24-28, 2012, IEEE Xplore, 2012.*

English machine tranlsation of Wang, CN 105213433 A, 2016.*

* cited by examiner

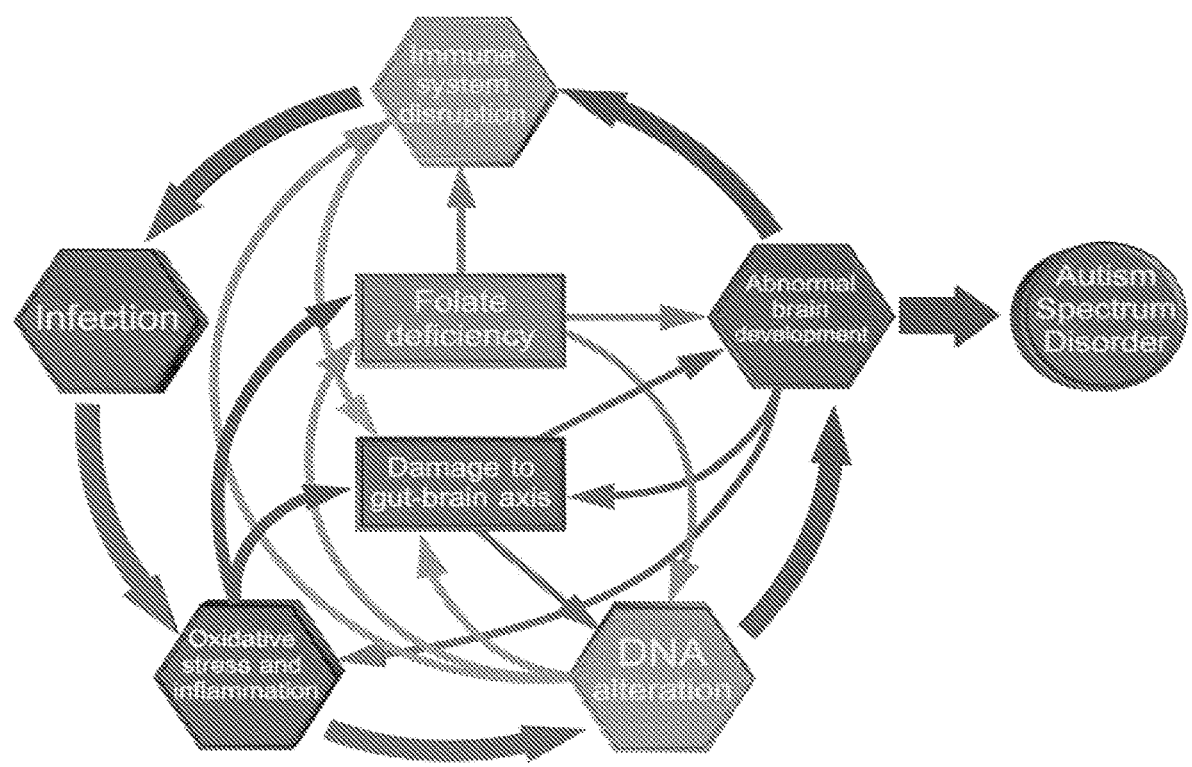

COMPOSITIONS AND METHODS FOR DIAGNOSING SUSCEPTIBILITY TO AUTISM SPECTRUM DISORDER (ASD), REDUCING THE LIKELIHOOD OF DEVELOPING ASD, AND/OR TREATING ASD

CROSS-REFERENCE TO RELATED APPLICATION

This application is a National Stage Application of International Application No. PCT/US2018/048571, filed Aug. 29, 2018; which claims priority to U.S. Provisional Patent Application, Ser. No. 62/551,557, filed Aug. 29, 2017, which is incorporated herein by reference in its entirety.

BACKGROUND OF INVENTION

Autism spectrum disorder (ASD) refers to a group of neurodevelopment disorders, including autistic disorder (autism), Asperger syndrome, childhood disintegrative disorder, and pervasive developmental disorders, which are characterized by repetitive, distinctive patterns of behavior and difficulties with social communication and interaction. Subjects with ASD may have a combination of many symptoms and syndromes, which are typically present from early childhood and affect daily functioning.

Included within ASD is a wide range of symptoms, skills, and levels of functional disability. Some children and adults with ASD are fully capable of performing all activities of daily life, while others require substantial support to perform basic life functions and activities. Additionally, individuals with ASD may experience pathologic changes such as brain inflammation, gastrointestinal problems, immune system imbalance, lipid metabolism imbalance, and possible increased risk of cancer due to links between autism and mutations in cancer-associated genes and pathways.

The prevalence of ASD in children in the United States has been increasing rapidly over the past 50 years. At present, the rate of ASD prevalence is 1 case for every 59 children born. Compared to 2016, when it was 1 in 68 children; 2008, when it was 1 in 125 children; and 50 years ago, when it was 1 in 2500 children, the present statistics indicate that ASD prevalence is not only increasing, but actually doubling every ten years.

Considerably more males are affected with ASD than females. For some individuals, the core symptoms of ASD (i.e., impairments in communication and social interaction, and restricted/repetitive behaviors and interests) may improve with intervention and maturation; however, core deficits typically translate into varying developmental presentations that endure throughout the lifespan.

The exact cause of ASD development is not entirely clear, and the underlying root of ASD symptoms, such as damaged brain structures and impaired nerve connections, cannot be readily corrected by existing medications. However, drugs useful in treating other diseases with similar symptoms can be useful in managing ASD, though none have been approved by the FDA for treating ASD specifically.

It is known that ASD does have a strong genetic component, with heritability estimated to be as high as 90% in some studies. Identification of specific genetic risk variants has proved to be challenging, however, and many researchers suggest that there may be multiple pathways to the disorder, with prenatal and postnatal insult potentially contributing to its development in some instances. For example, certain metabolic and other maternal conditions (e.g., diabetes, hypertension, obesity and infection), as well as consumption of alcohol and certain medications (e.g., antidepressants) during pregnancy may be associated with increased risk of ASD in offspring.

Additionally, maternal immune malfunction during pregnancy, including chronic immune activation of microglia, may also cause some alterations in a child's brain. The connection is explained by possible upregulation of brain inflammatory cytokines resulting from immune activation in the mother, which then leads to presence of these cytokines in sera and frontal and cingulate cortices of the fetal brain. This is thought to affect the course of brain development, which may lead to ASD.

Much of the research into ASD etiology points to congenital chronic infections as a cause for development of the disorder. Many of these infections are viral, including Herpes Simplex Virus (HSV) 1 and 2, Human Herpes Virus (HHV) 6, Epstein-Barr Virus, Rubella virus, Measles virus, Cytomegalovirus (CMV), BK virus, JK virus, SV40 virus, and others.

For example, it was reported in 2005 that in the USA, approximately 40,000 children are born with congenital cytomegalovirus (CMV) infection, and Binda et al. found that congenital CMV was found 10 times more often in blood of children with ASD than in healthy children. Human herpes virus-6 was found in children with ASD 3.5 times more often than within healthy children. Epstein-Barr virus (EBV) was found in patients with multiple sclerosis and ASD. Congenital rubella syndrome caused by transmission of rubella virus from mother to fetus also strongly affects the brain development, and children with ASD are infected 200 times more often than healthy children. Additionally, the combination of three viruses: BK virus, JC virus and simian virus 40 was found two times more often in children with ASD than in healthy controls.

Furthermore, the roles of herpes simplex viruses (HSV) 1 and 2 in influencing the development of a number of neurodevelopmental disorders, including schizophrenia, Alzheimer's disease, epilepsy, and ASD have also been studied.

The mechanism by which viral infection may lead to autism is not yet clear. One theory is that, once a subject is infected, many viruses have the ability to localize in certain brain sections, or through infection elsewhere in the body, trigger disease in the central nervous system. This might in turn disturb normal brain development. The mechanism may also occur through immune responses in the mother while a fetus is developing, which may lead to weakening of the fetus's immune system and further lead to disturbances in brain development.

There is no cure for ASD, but current therapies and behavioral interventions exist, which are designed to improve certain symptoms of the disorder, however, most existing treatments focus on treating the brain and cognitive functions specifically, rather than the other potential underlying causes of ASD and its symptoms. For example, repetitive transcranial magnetic stimulation (rTMS) is a type of brain stimulation therapy that has been tested as a treatment tool for various neurological and psychiatric disorders, including migraines, strokes, Parkinson's disease, dystonia, tinnitus, depression, and auditory hallucinations, where a coils is placed near the patient's head to depolarize or hyperpolarize neurons of the brain. In particular, rTMS uses electromagnetic induction to induce weak, repetitive electrical currents using a rapidly changing magnetic field to cause activity in desired brain regions. While this may produce short-term relief from certain cognitive and brain-related symptoms, it does not treat, for example, compromised immune health underlying a neurodegenerative condition.

The ideal treatment plan for a subject diagnosed with ASD coordinates therapies and interventions that meet the specific needs of the individual, based on where he or she falls on the spectrum. Most health care professionals agree that the earlier the intervention, the better.

Thus, there is a continuing need for new, integrated compositions and methods for treating a broad range of ASD symptoms and improving the overall quality of life and performance for patients-particularly children-diagnosed with autism and its spectra.

BRIEF SUMMARY

The present invention provides compositions and methods for identifying individuals at risk for developing autism spectrum disorder (ASD), for reducing the likelihood of developing ASD, and for treating people with ASD. Advantageously, embodiments of the present invention provide compositions and methods for improving the quality of life for subjects, particularly children, who have developed, or who are at risk for developing, ASD.

The materials and methods of the subject invention are based, in part, on the identification of the etiological progression associated with the development of ASD, including the identification of a sequence of alterations and damage to different physiological systems and organs in a subject. These alterations and damage lead to the development, progression, and perpetuation of ASD, and associated symptoms and conditions.

Specifically described herein is an infectious etiology wherein, first, a fetus is exposed to a pathogen, such as a virus or bacteria, or the fetus is exposed to maternal factors associated with the mother having been exposed to a pathogen. This exposure of the fetus to a pathogen and/or to deleterious immune system factors, induces inflammation and/or other deleterious immune responses in the fetus, which then elicit oxidative stress and/or pro-inflammatory factors that can cause DNA alterations, folate deficiency and/or damage to the gut-brain axis in the fetus or newborn child. These alterations cause abnormal brain development in the fetus and/or child and ultimately result in ASD. Further, these physiological changes compromise the immune system of the subject such that the subject cannot effectively fight the persistent infection, and the cycle repeats itself causing progression and perpetuation of autistic symptoms and ASD-related disorders.

In one embodiment, the method of the subject invention comprises testing a subject for, and/or diagnosing the subject with, ASD and/or a risk marker, as identified herein. The risk markers may be, for example, a viral infection or an immune system response to a viral infection. In one embodiment, the method can comprise testing the subject for signs of poor immune health by, for example, testing the subject for immune markers such as T-cells and natural killer (NK) cells. The testing can be performed using known testing methods.

In another embodiment, the subject invention comprises testing a woman who is pregnant, or who plans to become pregnant, for the ASD risk markers as identified herein. As with the risk markers for the child, the risk markers for which the woman can be tested include, but are not limited to, a pathogenic infection and/or an immune system response that is consistent with a pathogenic infection.

In one embodiment, an expectant mother, the fetus, and/or a child, who has tested positive for one or more risk markers for ASD can be treated in order to reduce the likelihood of the child developing ASD. The treatment can be, for example, the administration of an antibiotic, an antiviral, an anti-inflammatory compound, an anti-oxidant, a probiotic, an immunomodulatory compound and/or folate. The antiviral may be, for example, an antiviral agent such as valacyclovir or ganciclovir.

In certain embodiments, the subject being treated according to the present invention has previously contracted an infection, currently has an infection, or has been exposed to one or more infectious agents. In specific embodiments, the infection is due to a chronic virus.

In certain embodiments, the subject is infected with one or more of cytomegalovirus, Epstein-Barr virus, rubella virus, measles virus, herpes simplex type 1 or 2, herpes zoster, other herpes family viruses, or any other chronic, congenital, persistent, latent, dormant, acute and/or subacute viral infection.

The subject of the present invention can be any human. In one embodiment, the subject is a child or adolescent, for example, 16 years of age or younger.

Advantageously, the practice of the present invention can improve the quality of life for subjects who are diagnosed with, for example, ASD and/or a viral infection associated with ASD. The present invention can lead to improvement of mental, emotional and physiological symptoms of ASD, and/or improvement in behavioral performance.

BRIEF DESCRIPTION OF THE FIGURE

FIG. 1 shows the circular etiology and pathogenesis of ASD.

DETAILED DISCLOSURE

The present invention provides compositions and methods for identifying individuals at risk for developing autism spectrum disorder (ASD), for reducing the likelihood of developing ASD, and for treating people with ASD. Advantageously, embodiments of the present invention provide compositions and methods for improving the quality of life for subjects, particularly children, who have developed, or who are at risk for developing, ASD.

The materials and methods of the subject invention are based, in part, on the identification of the etiological progression associated with the development of ASD, including the identification of a sequence of alterations and damage to different physiological systems and organs in a subject. These alterations and damage lead to the development, progression, and perpetuation of ASD, and associated symptoms and conditions.

In accordance with the subject invention, ASD has been determined to be of infectious origins caused by any one or more of a variety of infectious agents. The infections are congenital in nature resulting from, for example, maternal infections. These infections trigger inflammatory changes including the generation of reactive species and other mediators. These mediators can cause damage to the DNA of the subject's brain, which then produces organic changes in the brain. Both inflammation and DNA damage then induce disruption of the immune system. Further, inflammation causes folate deficiency, which participates in the brain malfunction, all of which leads to ASD.

As shown in FIG. 1, the mechanisms playing roles in ASD development are interconnected. In many instances, the sequence of events in ASD starts with an infection that triggers the chain of events finally resulting in ASD. The infection may be, for example, passed from a pregnant mother to an unborn fetus.

Specifically described herein is an infectious etiology wherein, first, a fetus is exposed to a pathogen, such as a virus or bacteria, or the fetus is exposed to maternal factors associated with the mother having been exposed to a pathogen. This exposure of the fetus to a pathogen and/or to deleterious immune system factors, induces inflammation and/or other deleterious immune responses in the fetus, which then elicit oxidative stress and/or pro-inflammatory factors that can cause DNA alterations, folate deficiency and/or damage to the gut-brain axis in the fetus or newborn child. These alterations cause abnormal brain development in the fetus and/or child and ultimately result in ASD. Further, these physiological changes compromise the immune system of the subject such that the subject cannot effectively fight the persistent infection, and the cycle repeats itself causing progression and perpetuation of autistic symptoms and ASD-related disorders.

ASD is not just triggered and promoted by the events/ changes depicted in FIG. 1, but also, because they are interconnected, these factors have a "circularly closed" character that perpetuates the condition. Thus, the initial infection or infections, triggering the events leading to ASD, through a number of alterations, perpetuate ASD because of the inability of the subject's compromised immune system to effectively fight the infection.

The process of ASD symptom development is "continuous" by nature because the disrupted immune system is not capable of eliminating the infection, which additionally "feeds" the ASD process.

In one embodiment, the method of the subject invention comprises testing a subject for, and/or diagnosing the subject with, ASD and/or a risk marker, as identified herein. The risk markers may be, for example, a viral infection or an immune system response to a viral infection. In one embodiment, the method can comprise testing the subject for signs of poor immune health by, for example, testing the subject for immune markers such as T-cells and natural killer (NK) cells. The risk markers may also be genetic markers and/or family history. The testing can be performed using known testing methods.

In another embodiment, the subject invention comprises testing a woman who is pregnant, or who plans to become pregnant, for the ASD risk markers as identified herein. As with the risk markers for the child, the risk markers for which the woman can be tested include, but are not limited to, a pathogenic infection and/or an immune system response that is consistent with a pathogenic infection. Genetic testing and/or family history evaluation can also be done.

In one embodiment, an expectant mother, the fetus, and/or a child, who has tested positive for one or more risk markers for ASD can be treated in order to reduce the likelihood of the child developing ASD. The treatment can be, for example, the administration of an antibiotic, an antiviral, an anti-inflammatory compound, an anti-oxidant, a probiotic, an immunomodulatory compound and/or folate. The antiviral may be, for example, an antiviral agent such as valacyclovir or ganciclovir.

In certain embodiments, the subject being treated according to the present invention has previously contracted an infection, currently has an infection, or has been exposed to one or more infectious agents. In specific embodiments, the infection is due to a chronic virus.

In certain embodiments, the subject is infected with one or more of cytomegalovirus, Epstein-Barr virus, rubella virus, measles virus, herpes simplex type 1 or 2, herpes zoster, other herpes family viruses, or any other chronic, congenital, persistent, latent, dormant, acute and/or subacute viral infection.

The subject of the present invention can be any human. In one embodiment, the subject is a child or adolescent, for example, 16 years of age or younger.

Advantageously, the practice of the present invention can improve the quality of life for subjects who are diagnosed with, for example, ASD and/or a viral infection associated with ASD. The present invention can lead to improvement of mental, emotional and physiological symptoms of ASD, and/or improvement in behavioral performance.

In view of this ASD cycle, treatment according to the subject invention focuses on interrupting the cycle at various points. The interruption of the cycle may be, for example, in the form of treating an infection in the mother, the fetus, or a child. Treatment for the infection can include, for example, one or more of administering antibiotics or antiviral agents, and boosting the immune system.

The antiviral compound can be, for example, a prescription drug and/or naturally-derived treatments. Preferably, the antiviral compound is a drug selected from common drug compounds valacyclovir, acyclovir, famciclovir, ganciclovir, valganciclovir, ribavirin, brivudin, cidofovir, fomivirsen, foscarnet, penciclovir, vidarabine and others used to treat chronic, congenital, persistent, latent, dormant, acute and/or subacute viral infections.

The immune system can be boosted by, for example, the administration of immunomodulatory compositions, the use of anti-oxidants, and/or the administration of probiotics.

In one embodiment, the treatments of the subject invention can be combination treatments where, for example, an antiviral agent is administered with, for example, a folate or folic acid supplement, and/or a supplement composition that boosts immune system health and/or provides additional antiviral and/or antibiotic activity.

The present invention provides compositions and methods for treating subjects with an autism spectrum disorder (ASD) and/or an immunocompromising condition. Advantageously, the subject invention can improve the immune health and overall quality of life of a subject-particularly a child—diagnosed with ASD and/or an immunocompromising condition. In one embodiment, the method can be used to treat ASD and its symptoms, including behavioral, mental, emotional and/or physiological symptoms.

Selected Definitions

The terms "autism spectrum disorder" and "ASD" are used in this disclosure to refer to a spectrum of disorders characterized by abnormalities of social interactions and communication, as well as restricted interests and repetitive behavior. This spectrum includes, but is not limited to, autistic disorder (autism), Asperger's syndrome, childhood disintegrative disorder, atypical autism or pervasive developmental disorder not otherwise specified (PPD-NOS), as well as Rett syndrome and tuberous sclerosis.

As used herein, "treating" or "treatment" means the eradicating, improving, reducing, ameliorating or reversing of at least one sign or symptom of a condition or disorder. Treatment can include, but does not require, a complete cure of the condition or disorder, meaning treatment can also include partial eradication, improvement, reduction, amelioration or reversal. Treatment can also include delaying, forestalling and/or inhibiting the progression of a condition or disorder to a more severe condition or disorder.

Signs and/or symptoms of ASD encompass those of ASD or of any comorbidity of ASD. Signs and symptoms associated with ASD include, but are not limited to irritability; hyperactivity; inattention; abnormalities in speech, verbal, communication, and language skills; repetitive behavior, including stereotypy, compulsive behavior, sameness (resistance to change), and ritualistic behavior, obsessive focus on certain topics and/or objects; inability to make eye contact; abnormalities in social interactions and/or understanding of others' feelings; anger issues and/or emotional outbursts; self-injury; and others.

Comorbidities of ASD include but are not limited to anxiety; attention deficit disorder, brain inflammation; viral infections; clinical depression; Tourette syndrome; Fragile X syndrome; obsessive-compulsive disorder, bipolar disorder; learning disabilities; sensory disorders; developmental coordination disorder, disorders of the immune system and/or gastrointestinal system, including candidiasis; seizures and/or epilepsy; sleep disorders; increased risk of cancer, and others.

The terms "therapeutically effective" amount or dose, "effective amount," and "effective dose" are used in this disclosure to refer to an amount of a method, compound or composition that, when administered to a subject, is capable of providing a desired therapeutic effect or a desired level or treatment. The actual amount of the method, compound or composition will vary depending on a number of factors including, but not limited to, the particular disorder being treated, the severity of the disorder, the size and health of the patient, and the route of administration. A skilled medical practitioner can readily determine the appropriate amount using methods known in the medical arts.

A plant "extract," as used herein, refers to the material resulting from exposing a plant part to a solvent and removing the solvent, or from using various chemical, immunological, biochemical or physical procedures known to those of skill in the art, including but not limited to, precipitation, centrifugation, filtering, column chromatography, and detergent lysis. Plant material can include roots, stems, leaves, flowers, or parts thereof.

As used herein, the term "probiotic" refers to microorganisms, which, when administered in adequate amounts, confer a health benefit on the host. The probiotics may be available in foods and dietary supplements (for example through capsules, tablets, and powders). Non-limiting examples of foods containing probiotics include dairy products such as yogurt, fermented and unfermented milk, smoothies, butter, cream, hummus, kombucha, salad dressing, miso, tempeh, nutrition bars, and some juices and soy beverages. In preferred embodiments, the microorganisms are live.

The terms "natural" and "naturally-derived," as used in the context of a chemical compound or substance is a material that is found in nature, meaning that it is produced from earth processes or by a living organism. A natural product can be isolated or purified from its natural source of origin and utilized in, or incorporated into, a variety of applications, including foods, beverages, cosmetics, and supplements. A natural product can also be produced in a lab by chemical synthesis, provided no artificial components or ingredients (i.e., synthetic ingredients that cannot be found naturally as a product of the earth or a living organism) are added.

The terms "isolated" or "purified," when used in connection with biological or natural materials such as nucleic acid molecules, polynucleotides, polypeptides, proteins, organic compounds, such as small molecules, microorganism cells/strains, or host cells, means the material is substantially free of other compounds, such as cellular material, with which it is associated in nature. That is, the materials do not occur naturally without these other compounds and/or have different or distinctive characteristics compared with those found in the native material.

In certain embodiments, purified compounds are at least 60% by weight the compound of interest. Preferably, the preparation is at least 75%, more preferably at least 90%, and most preferably at least 99% or 100% (w/w) of the desired compound by weight. Purity is measured by any appropriate standard method, for example, by column chromatography, thin layer chromatography, or high-performance liquid chromatography (HPLC) analysis.

The description herein of any aspect or embodiment of the invention using terms such as "comprising," "having," "including," or "containing" with reference to an element or elements is intended to provide support for a similar aspect or embodiment of the invention that "consists of," "consists essentially of," or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The term "consisting essentially of," as used herein, limits the scope of the ingredients and steps to the specified materials or steps and those that do not materially affect the basic and novel characteristic(s) of the present invention.

Supplement Compositions

In certain embodiments, the present invention provides a supplement composition for improving the quality of life for a subject diagnosed with ASD, wherein the supplement composition comprises ingredients that help support immune health and suppress infectious agents in the subject's body. Preferably, a majority, if not all, of these ingredients can be natural or naturally-derived.

In one embodiment, the supplement composition comprises L-lysine, Elderberry extract, olive leaf extract, *Astragalus* root extract, and *Bacillus coagulans* GBI-30 probiotic (BC30).

In a further embodiment the supplement composition comprises, consists of, or consists essentially of L-lysine, Elderberry extract, olive leaf extract, *Astragalus* root extract, and *Bacillus coagulans* BC30.

In one embodiment, the supplement composition helps support the immune system of a subject with a compromised immune system, for example, a subject diagnosed with ASD and/or a viral infection. As used herein, the term "support" can include boosting, improving, enhancing, and/or maintaining the proper functioning of a body system, for example, those involved in the immune system.

Immune support can include support for the cells, tissues, and organs that contribute to proper functioning of the immune system, for example, the lymphatic system, spleen, bone marrow, or any other system involved in production of entities (e.g., antibodies, lymphocytes, red blood cells, white blood cells, platelets) that ward off foreign substances (e.g., inoculants such as bacteria, viruses, parasites, and fungi) from the body's normal and healthy tissues. Immune support can further include support for parts of the body that aid in preventing and healing from injury, inflammation, cancer, or other non-infectious diseases, ailments, or conditions.

In some aspects, the supplement composition can also help support other body systems that are known to be interrelated with immune health, such as the circulatory, endocrine, urinary, muscular, respiratory, skeletal, central nervous, digestive, integumentary, and reproductive systems. In other words, the subject composition can be effective in supporting more than one body system, particularly where the health of one body system promotes the health of another.

In one embodiment, L-lysine is present in the supplement composition in amounts up to 750 mg, up to 500 mg, up to 250 mg or up to 125 mg.

L-lysine is an essential amino acid found naturally in, for example, meats, beans, cheeses, eggs and other casein-containing foods. It is important for proper growth, muscle protein building and metabolism, and can be effective in reducing anxiety, mood disturbances and headaches. Furthermore, L-lysine reduces the cyto-pathogenicity of HSV through reduction in the herpes virus load.

In one embodiment, Elderberry extract is present in the supplement composition in amounts up to 750 mg, up to 500 mg, up to 250 mg or up to 125 mg.

Elderberry extract comprises extract from the fruit and/or flowers of plants of the black elder plant (*Sambucus nigra*). It is a well-known immune-boosting substance containing anthocyanins, flavonoids, vitamins, minerals and antioxidants. Elderberry extract has been shown to alleviate allergies, protect against certain infections such as cold and flu viruses, reduce toothaches and headaches, moderate digestion, and exhibit activity against HSV 1. Furthermore, the flavonoids and anthocyanins in elderberry extract provide anti-inflammatory, anti-oxidant and immunostimulatory properties.

In one embodiment, olive leaf extract (*Olea europaea*) is present in the composition in amounts up to 750 mg, up to 500 mg, up to 250 mg or up to 125 mg.

Olive leaf extract is well known as a multi-functional alternative treatment for many diseases and conditions. The chemical compounds found in olive leaf extracts, including polyphenols, flavonoids, oleuropein, tyrosol, and hydroxytyrosol, and more particularly the active ingredient elenolic acid, have antibacterial, antioxidant, antiviral, neuroprotective and antifungal properties, thereby making olive leaf extract effective in fighting a wide range of diseases, including: influenza, EBV, CMV, common cold, bacterial/viral meningitis, postsurgical infections, kidney infections, shingles, hepatitis, pneumonia and malaria. Additionally, olive leaf can affect the down-regulation of genes that participate in inflammatory processes, thus making it a useful anti-inflammatory compound. Furthermore, olive leaf extract is through to be effective for regulation of lipid and carbohydrate metabolism as well as hypoglycemia.

In one embodiment, *Astragalus* root extract is present in the composition in amounts up to 750 mg, up to 500 mg, up to 250 mg or up to 125 mg.

*Astragalus* root extract can be obtained from the roots of an *Astragalus* plant species, including, for example, *Astragalus membranaceus*. This extract has antibacterial, antiviral, anti-inflammatory, antioxidant, anti-aging, and anti-cancer properties. Furthermore, *Astragalus* intake enhances production of immune system cells and stimulation of growth of stem cells.

In one embodiment, *Bacillus coagulans* GBI-30 probiotic (BC30) is present in the composition in amounts from $1 \times 10^8$ to $1 \times 10^{12}$ CFU, preferably from $1 \times 10^9$ to $1 \times 10^{11}$ CFU, and more preferably 2 billion CFU.

BC30 has been shown to promote digestive health, aide in reducing inflammation, and regulate imbalances in lipid metabolism and the immune system. Moreover, BC30 intake can increase immune response to viral agents, such as influenza A virus and adenovirus and inhibit some herpes family viruses.

BC30 is a preferred probiotic for the present invention because it is capable of surviving the acidity of the stomach, thus allowing it to reach the intestines. BC30 contains a natural protective layer of proteins, which allows it to not only survive the harsh environment of the stomach, but also allows it to survive most manufacturing processes. Moreover, BC30 may also out-compete other harmful bacteria that cause infections or may have other deleterious effects. BC30 may delay the onset of symptoms and promote quicker recovery from infection and/or colitis caused by *Clostridium dificile*. BC30 may also be helpful in replenishing beneficial bacteria in the intestines for individuals who have been prescribed antibiotics.

Formulation and Delivery of Supplement Compositions

In a preferred embodiment, the supplement composition of the present invention is formulated so that it can be delivered to a subject orally. In particular, the composition is formulated as an orally-consumable product.

Orally-consumable products according to the invention are any preparations or compositions suitable for consumption, for nutrition, for oral hygiene or for pleasure, and are products intended to be introduced into the human or animal oral cavity, to remain there for a certain period of time and then to either be swallowed (e.g., food ready for consumption) or to be removed from the oral cavity again (e.g. chewing gums or products of oral hygiene or medical mouth washes). These products include all substances or products intended to be ingested by humans or animals in a processed, semi-processed or unprocessed state. This also includes substances that are added to orally-consumable products (e.g., active ingredients such as extracts, nutrients, supplements, or pharmaceutical products) during their production, treatment or processing and intended to be introduced into the human or animal oral cavity.

Orally-consumable products can also include substances intended to be swallowed by humans or animals and then digested in an unmodified, prepared or processed state. These include casings, coatings or other encapsulations that are intended also to be swallowed together with the product or for which swallowing is to be anticipated.

Preferably, the orally-consumable product according to the invention is formulated as a composition to be consumed for nutrition or pleasure. These particularly include baked goods (e.g., bread, dry biscuits, cake, cookies, brownies and other pastries), sweets and candies (e.g., chocolates, chocolate bar products, other bar products, gummies, fruit leathers, jelly beans, coated tablets, hard candies, toffees and caramels, and chewing gum), non-alcoholic beverages (e.g., cocoa, coffee, green tea, black tea, herbal teas, lemonades, isotonic beverages, soft drinks, nectars, fruit and vegetable juices, and fruit or vegetable juice preparations), instant beverages (e.g., instant cocoa beverages, instant tea beverages, instant smoothies, instant milkshakes and instant coffee beverages), meat products (e.g., cold cuts, fresh or raw sausage preparations, seasoned oder, marinated fresh meat or salted meat products), eggs or egg products (e.g., dried whole egg, egg whites, and egg yolks), cereal products (e.g., breakfast cereals, muesli bars, and pre-cooked instant rice products), dairy products (e.g., whole fat or fat reduced or fat-free milk beverages, rice pudding, yoghurt, kefir, cream cheese, soft cheese, hard cheese, dried milk powder, ice cream, sherbet, whey, butter, buttermilk, and partly or wholly hydrolyzed products containing milk proteins), products produced from nuts (e.g., nut milks, nut butters, nut flours or powders), products from soy protein or other soy bean fractions (e.g., soy milk and products prepared thereof, beverages containing isolated or enzymatically treated soy protein, soy flour containing beverages, preparations containing soy lecithin, fermented products such as tofu or tempeh products prepared thereof and mixtures with fruit preparations and, optionally, flavoring substances), fruit preparations (e.g., jams, fruit ice cream, fruit sorbets, fruit smoothies, fruit sauces, and fruit fillings), vegetable preparations (e.g., ketchup, sauces, dried vegetables, deep-freeze vegetables, pre-cooked vegetables, and boiled vegetables), snack articles (e.g., chips, crisps, pretzels, biscuits, crackers and nuts), products on the basis of fat and oil or emulsions thereof (e.g., mayonnaise, remoulade, and dressings), other ready-made meals and soups (e.g., dry soups, instant soups, and pre-cooked soups), seasonings (e.g., sprinkle-on seasonings), sweetener compositions (e.g., tablets, sachets, and other preparations for sweetening beverages or other food). The present compositions may also serve as semi-finished products for the production of other compositions intended for nutrition or pleasure.

Preferably, the present composition is delivered by an orally-consumable product that appeals to children, for example, in the form of a sweet treat or snack. In a preferred embodiment, the composition is delivered in the form of a chocolate bar, a gummy or a jelly.

When formulated as a chocolate bar, the chocolate can be dark chocolate, light chocolate, milk chocolate, white chocolate or a mixture thereof. Optionally, caramel, nut butters, fruit or fruit fillings, coconut, sprinkles, chips (chocolate or other), candies, or any of a variety of other flavorings or food products can be added to the bar to enhance the taste and appeal thereof.

Preferably, the chocolate bars are packaged in blister packs, or in larger, multi-dose break-apart bars with individual sections constituting one dose. The chocolate bars can also be packaged as individually wrapped single-dose bars.

In certain embodiments, the composition is formulated as a gummy or a jelly, or some other form of gelatinous or chewy candy. For example, the composition can be formulated as a gummy bear, gummy worm, or other well-known gummy candy, a fruit snack, a fruit tape, a fruit leather, a jelly bean or a taffy. A single dose of the supplement composition can be included in one piece of the candy, or divided between a pre-determined number of candies, for example from 2 to 5 pieces.

The composition of the subject invention can also be present in the form of capsules, tablets (uncoated and coated tablets, e.g., gastro-resistant coatings), coated tablets, granules, pellets, solid-substance mixtures, dispersions in liquid phases, as emulsions, powders, solutions, pastes or other swallowable or chewable preparations, or as a dietary supplement.

For oral administration, tablets or capsules can be prepared by conventional means with acceptable excipients such as binding agents, fillers, lubricants, disintegrants, or wetting agents. The tablets can be coated, if desired. Liquid preparations for oral administration can take the form of, for example, solutions, syrups, or suspension, or they can be presented as a dry product for constitution with saline or other suitable liquid vehicle before use.

The compositions described herein can also contain acceptable additives as will be understood by one skilled in the art, depending on the particular form of the delivery method. Non-limiting examples of such additives include suspending agents, emulsifying agents, non-aqueous vehicles, preservatives, buffer salts, flavoring, coloring, and sweetening agents as appropriate. Non-limiting examples of specific additives include: gelatin, glycerin, water, beeswax, lecithin, cocoa, caramel, titanium dioxide, and carmine. Preparations for oral administration also can be suitably formulated to give controlled release of the active ingredients.

In some cases, the composition provided herein can contain an acceptable carrier for administration to a human subject or other mammal including, without limitation, sterile aqueous or non-aqueous solutions, suspensions, and emulsions. Examples of non-aqueous solvents include, without limitation, propylene glycol, polyethylene glycol, vegetable oils, and organic esters. Aqueous carriers include, without limitation, water, alcohol, saline, and buffered solutions. Acceptable carriers also can include physiologically acceptable aqueous vehicles (e.g., physiological saline) or other known carriers appropriate to specific routes of administration.

Methods for Reducing the Likelihood of Developing ASD and/or Improving the Quality of Life in ASD Subjects The present invention provides methods for reducing the likelihood of developing Ask and/or improving the quality of life for a subject diagnosed with ASD or who has tested positive for a risk marker of ASD, wherein the method comprises administering to the subject a therapeutically-effective dose of a composition that interrupts some aspect of the cycle shown in FIG. 1. The composition may be, for example, an antibiotic, an antiviral, an anti-inflammatory, a DNA protectant, an immunomodulator, a folate supplement, and/or a supplement composition of the present invention.

Advantageously, the present invention can improve the quality of life for subjects who are diagnosed with, for example, ASD and/or an infection. In other words, the present invention can lead to simultaneous improvement of, for example, the mental, emotional and physiological symptoms of ASD, improvement in behavioral performance, improvement in the signs and symptoms of infections, and improvement in the overall immune health of the subject.

In one embodiment, the method can be used to improve symptoms of ASD, including behavioral, mental, emotional and/or physiological symptoms.

The subject of the present invention can be any human diagnosed with ASD or exhibiting the signs, symptoms and/or risk markers thereof. In one embodiment, the human subject is a child or adolescent, for example, 16 years of age or younger.

In some embodiments, the subject is a fetus of a pregnant woman. In such cases, and the method comprises administering the composition to the pregnant woman.

In one embodiment, the subject is a child diagnosed with ASD or who exhibits the signs and symptoms thereof. In another embodiment, the subject has a compromised immune system, for example, due to genetics, illness, or because the subject previously contracted or was exposed to a viral or bacterial infection. The subject may presently be exhibiting signs of infection, or the subject may be asymptomatic because, for example, contraction of the virus occurred at some time in the past, e.g., in utero.

In specific embodiments, the subject has contracted or been exposed to a viral infection thought to be associated with alteration of immune system functioning and/or development of ASD, including but not limited to the following long-term or chronic viruses: cytomegalovirus (CMV); Rubella virus; measles virus; varicella zoster virus (VZV);

Epstein-Barr virus (EBV), herpes simplex virus types 1 and 2 (HSV); human herpes virus (HHV); BK virus (BKV); JC virus (JCV); and simian virus 40 (SV40).

Viral infection or exposure according to the subject disclosure typically occurs early on in a subject's development, either through vertical transmission (i.e., from mother to embryo, fetus, or infant during pregnancy or childbirth), direct transmission (i.e., contact from another infected subject), or indirect transmission (e.g, through a vector).

In some embodiments, the method comprises the step of diagnosing the subject with ASD prior to administering the antiviral to the subject. In further embodiments, the method comprises, the step of testing the subject for infection or signs of exposure to an infection prior to administering the antiviral to the subject. This can be done using, for example, blood tests that detect certain antibodies. In one embodiment, the method can also comprise performing an immune analysis on the subject to test for overall immune health and/or the presence of any immunocompromising conditions.

According to one embodiment, the step of administering antiviral treatment comprises administering a therapeutically-effective dose of a prescription antiviral medication. The antiviral compound according to the subject methods can include prescription drugs and/or naturally-derived treatments. Preferably, the antiviral compound is a prescription drug selected from the commonly used drug compounds valacyclovir, acyclovir, famciclovir, ganciclovir, valganciclovir, ribavirin, brivudin, cidofovir, fomivirsen, foscarnet, penciclovir, vidarabine and others used to treat chronic, congenital, persistent, latent, dormant, acute and/or subacute viral infections.

In one embodiment, the antiviral medication is selected from the group consisting of valacyclovir (also known as Valtrex), acyclovir (also known as Zovirax), ganciclovir (also known as, e.g., Cytovene) and famciclovir (also known as Famvir).

Each of these commercially available drugs was originally designed for treatment of adults infected with herpes family viruses. Valacyclovir, most commonly administered for treating and suppressing genital herpes, can be given to patients with ASD to suppress the herpes virus, if present, and decrease inflammation and neurological dysfunction it causes. Valacyclovir can also be useful in managing and/or treating herpes zoster (shingles), cytomegalovirus, EBV, mononucleosis, and herpes B.

Valacyclovir is the prodrug of acyclovir, another common antiviral treatment. Acyclovir differs from valacyclovir in that it typically requires more frequent dosage.

Children with ASD may show improvements in any aspect of their spectrum of symptoms in response to treatment with these antiviral medications, including but not limited to improvement in behavioral performance.

In embodiments of the present invention, administration of the antiviral medication occurs daily for several months or longer. Administration can include any known method of drug administration, including, but not limited to, oral, nasal, cutaneous (e.g., applying it as a cream), or intravenous administration. In preferred embodiments, administration is performed orally once or twice daily.

The medication can be administered in cycles, for example, four months on with two months off, or three weeks on with one week off. Cycles can be repeated multiple times, for example three times, or as many times as deemed necessary by a skilled physician.

In a preferred embodiment, the antiviral treatment is valacyclovir. Valacyclovir can be administered to the subject once or twice a day, at up to 500 mg per dose, up to 250 mg per dose or up to 125 mg per dose. Proper dosage of the antiviral treatment is determined by a skilled physician based on the individual receiving treatment, with factors such as age and symptoms considered.

In preferred embodiments, at the start of treatment, the antiviral compound is administered to the subject on its own for one week, two weeks or three weeks, to determine whether the subject will experience any adverse side-effects from the medication. Then, the supplement composition can be introduced into the treatment while the antiviral treatment is continued.

In one embodiment, the supplement composition is ingested by the subject once, twice, or three times per day, determined on a subject-by-subject basis by a skilled physician. Factors to be considered when determining the number of doses to administer include the age of the individual receiving treatment and the severity of his/her symptoms.

The concomitant administration of antiviral and supplement composition can be continued for one or more consecutive cycles lasting, for example, 21 days or longer. A cycle can be repeated as many times as necessary without breaking in between, for example, 3 times or more. In one embodiment, the antiviral treatment can be discontinued after a certain number of cycles, and administration of the supplement composition can optionally be continued indefinitely.

In one embodiment, the method comprises administering a supplement composition comprising L-lysine, Elderberry extract, olive leaf extract, *Astragalus* root extract, and *Bacillus coagulans* GBI-30 probiotic (BC30).

In another embodiment, the method comprising administering a supplement composition comprising, consisting of, or consisting essentially of L-lysine, Elderberry extract, olive leaf extract, *Astragalus* root extract, and *Bacillus coagulans* GBI-30 probiotic (BC30).

More specifically, the method can comprise administering L-Lycine in amounts up to 750 mg, up to 500 mg, up to 250 mg or up to 125 mg; Elderberry extract in amounts up to 750 mg, up to 500 mg, up to 250 mg or up to 125 mg; olive leaf extract in amounts up to 750 mg, up to 500 mg, up to 250 mg or up to 125 mg; *Astragalus* root extract in amounts up to 750 mg, up to 500 mg, up to 250 mg or up to 125 mg; and *Bacillus coagulans* GBI-30 probiotic (BC30) in amounts up to 2 billion CFUs.

In one embodiment, the amount of each of L-lysine, Elderberry extract, olive leaf extract, and *Astragalus* root extract is from about 125 mg to about 750 mg, from about 125 mg to about 500 mg, and/or from about 125 mg to about 250 mg. In one embodiment, the amount of BC30 is from about $1 \times 10^8$ CFU to about $1 \times 10^{12}$, from about $1 \times 10^9$ to about $1 \times 10^{11}$ CFU, or about 2 billion CFU.

In one embodiment, the subject undergoes periodic blood work throughout the treatment time period, for example every week, every month, or every two months. The blood testing can not only be used to monitor the level of, for example, viral antibodies and/or viral load in a subject, but also monitor how the subject's liver, kidneys, blood cells and other body functions are operating. These tests can serve as precautionary safeguards, as harmful side effects from these treatments are rare or even nonexistent.

In some embodiments, the methods disclosed herein can also include measuring a baseline of behavioral performance and/or overall health prior to treatment of the subject according to the subject methods, and/or measuring the behavioral performance and/or overall health after treatment. The methods can include comparing the behavioral performance and/or overall health prior to and after treatment is administered to the subject, and the comparison can be used to determine if and to what extent the behavioral performance and/or overall health in the subject is improved, or if adjustments should be made to the treatment given.

As used herein, the phrase "improvement in behavioral performance" refers to reduction in the severity or frequency, to whatever extent, of one or more of the behavioral disorders, symptoms and/or abnormalities expressed by an individual suffering from ASD, or a pathological condition having behavioral symptoms similar to those of ASD. The improvement is either observed by the individual taking the treatment themselves or by another person (medical professional or otherwise).

In the method disclosed herein, behavioral performance can be measured and evaluated using various parameters and methods. For example, behavioral tests can be conducted to determine the presence and/or extent of restricted repetitive behavior and/or stereotyped behavior patterns of the subject under test. In some embodiments, the Autism Behavior Checklist (ABC), Autism diagnostic Interview-Revised (ADI-R), childhood autism Rating Scale (CARS), and/or Pre-Linguistic Autism Diagnostic Observation Schedule (PL-ADOS) is used for the behavioral test. The behavioral test can include, but is not limited to, detecting the presence and/or extent of (1) preoccupation with one or more stereotyped and restricted patterns of interest that is abnormal in either intensity or focus; (2) inflexible adherence to specific, nonfunctional routines or rituals; (3) stereotyped and repetitive motor mannerisms (such as hand flapping, finger flapping etc.); and/or (4) persistent preoccupation with parts of objects. Non-limiting examples of behavior that can be included in a behavioral test and suggest a need for improving behavioral performance in the subject under the test include:

(a) Sensory behaviors: poor use of visual discrimination when learning; seems not to hear, so that a hearing loss is suspected; sometimes shows no "startle response" to loud noise; sometimes painful stimuli such as bruises, cuts, and injections evoke no reaction; often will not blink when bright light is directed toward eyes; covers ears at many sounds, squints, frowns, or covers eyes when in the presence of natural light; frequently has no visual reaction to a "new" person; stares into space for long periods of time;

(b) Relating behaviors: frequently does not attend to social/environmental stimuli; has no social smile; does not reach out when reached for, non-responsive to others' facial expressions/feelings; actively avoids eye contact; resists being touched or held; is flaccid when held in arms; is stiff and hard to hold; does not imitate other children at play; has not developed any friendships; is often frightened or very anxious; "looks through" people;

(c) Body and object use behaviors: whirls self for long periods of time; does not use toys appropriately; insists on keeping certain objects with him/her, rocks self for long periods of time; frequently lunges and darts; flaps hands; walks on toes; hurts self by banging head, biting hand, etc.; twirls, spins, and bangs objects frequently; will feel, smell, and/or taste objects in the environment; performs complicated "rituals" such as lining things up; is very destructive; and (d) Language behaviors: does not follow simple commands given once; has pronoun reversal; speech is atonal; does not respond to own name when called out among others; seldom says "yes" or "I"; does not follow simple commands involving prepositions; uses gestures to get desired objects; repeats phrases over and over, cannot point to more than five named objects; uses 0-5 spontaneous words per day to communicate wants and needs; repeats sounds or words over and over, echoes questions or statements made by others; uses at least 15 but less than 30 spontaneous phrases daily to communicate; learns a simple task but "forgets" quickly; has strong reactions to changes in routine/environment; has "special abilities" in one area of development, which seems to rule out mental retardation; has severe temper tantrums and/or frequent minor tantrums; hurts others by biting, hitting, kicking, etc.; does not wait for needs to be met; has difficulties with toileting; does not dress self without frequent help; is frequently unaware of surroundings and may be oblivious to dangerous situations; prefers to manipulate and be occupied with inanimate things; and a developmental delay was identified at or before 30 months of age.

One of ordinary skill in the art would appreciate that the attending physician would know how to identify a subject in need of treatment disclosed herein.

We claim:

1. A method for treating Autism Spectrum Disorder (ASD) or for reducing the likelihood of a subject developing ASD in a subject in need thereof, the method comprising:
   a) diagnosing the subject with ASD, or, if the subject is a fetus of a pregnant woman, testing the pregnant woman for ASD, and,
   b) if ASD is diagnosed, treating the subject and/or the pregnant woman with an antibiotic agent or an antiviral agent and
   c) further treating the subject and/or the pregnant woman with a supplement composition comprising therapeutically effective amounts of:
      (i) L-lysine,
      (ii) Elderberry extract,
      (iii) olive leaf extract,
      (iv) *Astragalus* root extract, and
      (v) *Bacillus coagulans* GBI-30 probiotic (BC30).

2. The method of claim 1, wherein the subject is a child aged 16 years or younger.

3. The method of claim 1, wherein the subject or the pregnant woman is infected with a herpes family virus.

4. The method of claim 1, wherein the antiviral agent is valacyclovir or ganciclovir.

5. The method, according to claim 1, wherein the supplement composition consists essentially of:
   L-lysine,
   Elderberry extract,
   olive leaf extract,
   *Astragalus* root extract, and
   BC30.

6. The method of claim 1, wherein the supplement composition is delivered orally to the subject or the pregnant woman in the form of a chocolate bar, a gummy candy or a jelly candy.

7. The method of claim 1, wherein each of L-lysine, Elderberry extract, olive leaf extract, and *Astragalus* root extract is present in an amount from 125 mg to 750 mg.

8. The method of claim 1, wherein the amount of BC30 is $1\times10^8$ to $1\times10^{12}$ CFU.

9. The method of claim 1, wherein the subject is diagnosed with ASD.

10. The method of claim 1, wherein the subject was diagnosed with ASD and the method further comprises, after administering the antiviral or antibacterial agent, and the supplement composition, assessing the subject for improvement of the ASD.

* * * * *